(12) United States Patent
Oren et al.

(10) Patent No.: US 11,607,526 B2
(45) Date of Patent: Mar. 21, 2023

(54) RELIABILITY DETERMINATION OF ELECTRODE LOCATION DATA

(71) Applicant: St. Jude Medical International Holding S.à r.l., Luxembourg (LU)

(72) Inventors: Eitan Oren, Haifa (IL); Oded Sudarsky, Kfar Yedidya (IL); Adar Shlain, Hadar-Am (IL); Stavit Cohen, Kerem Maharal (IL); Alexander Zaslavsky, Kerem Maharal (IL); Silvina Rybnikov, Zichron Ya'acov (IL); Maxim Yoresh, Haifa (IL)

(73) Assignee: ST JUDE MEDICAL INTERNATIONAL HOLDINGS S.À R.L., Luxembourg (LU)

( * ) Notice: Subject to any disclaimer, the term of this patent is extended or adjusted under 35 U.S.C. 154(b) by 0 days.

(21) Appl. No.: 17/208,096

(22) Filed: Mar. 22, 2021

(65) Prior Publication Data
US 2021/0299405 A1 Sep. 30, 2021

Related U.S. Application Data

(63) Continuation of application No. 16/456,439, filed on Jun. 28, 2019, now Pat. No. 10,967,147.
(Continued)

(51) Int. Cl.
*A61M 25/01* (2006.01)
*A61B 90/00* (2016.01)
(Continued)

(52) U.S. Cl.
CPC ...... *A61M 25/0105* (2013.01); *A61B 1/00004* (2013.01); *A61B 17/00* (2013.01);
(Continued)

(58) Field of Classification Search
CPC ...... A61M 25/0105; A61M 2025/0166; A61B 90/06; A61B 90/08; A61B 1/00004;
(Continued)

(56) References Cited

U.S. PATENT DOCUMENTS 6,233,476 B1 5/2001 Strommer et al.
6,498,944 B1 12/2002 Ben-Haim et al.
(Continued)

*Primary Examiner* — Giovanni Astacio-Oquendo
(74) *Attorney, Agent, or Firm* — Billion & Armitage

(57) ABSTRACT

Embodiments of the present disclosure include a system for determining an error associated with an electrode disposed on a medical device. The system comprises a processor and a memory storing instructions on a non-transitory computer-readable medium. The instructions are executable by the processor to receive an electrode signal from the electrode disposed on the medical device. The instructions are further executable by the processor to receive a plurality of other electrode signals from a plurality of other electrodes disposed on the medical device. The instructions are further executable by the processor to determine that the electrode signal received from the electrode disposed on the medical device is an outlier in relation to the plurality of other electrode signals from the plurality of other electrodes disposed on the medical device, based on a comparison between the electrode signal and the plurality of other electrode signals.

20 Claims, 8 Drawing Sheets

Related U.S. Application Data

(60) Provisional application No. 62/691,275, filed on Jun. 28, 2018.

(51) Int. Cl.
  *A61B 1/00* (2006.01)
  *A61B 17/00* (2006.01)
  *G06T 5/00* (2006.01)
  *G06T 7/70* (2017.01)

(52) U.S. Cl.
  CPC .............. *A61B 90/06* (2016.02); *A61B 90/08* (2016.02); *G06T 5/002* (2013.01); *G06T 7/70* (2017.01); *A61B 2017/00026* (2013.01); *A61B 2090/067* (2016.02); *A61B 2090/0811* (2016.02); *A61M 2025/0166* (2013.01); *G06T 2207/30021* (2013.01)

(58) Field of Classification Search
  CPC ............ A61B 17/00; A61B 2090/0811; A61B 2090/067; A61B 2017/00026; A61B 2090/061; A61B 34/20; A61B 2034/2051; A61B 2017/00053; G06T 5/002; G06T 7/70; G06T 2207/30021; G06K 2209/057
  USPC ......................................... 324/649, 630, 600
  See application file for complete search history.

(56) References Cited

U.S. PATENT DOCUMENTS

| | | | |
|---|---|---|---|
| 6,690,963 | B2 | 2/2004 | Ben-Haim et al. |
| 6,788,967 | B2 | 9/2004 | Ben-Haim et al. |
| 7,197,354 | B2 | 3/2007 | Sobe |
| 7,263,397 | B2 | 8/2007 | Hauck et al. |
| 7,386,339 | B2 | 6/2008 | Strommer et al. |
| 8,636,718 | B2 | 1/2014 | Sela et al. |
| 10,874,462 | B2* | 12/2020 | Govari .................... H04L 43/04 |
| 11,471,094 | B2* | 10/2022 | Burns ................. A61M 5/1723 |
| 2006/0271119 | A1 | 11/2006 | Ni et al. |
| 2007/0100407 | A1 | 5/2007 | Armstrong |
| 2009/0030487 | A1 | 1/2009 | Lang |
| 2012/0078321 | A1* | 3/2012 | Blomqvist ......... A61N 1/36542 607/19 |
| 2017/0296056 | A1* | 10/2017 | Hresko |
| 2018/0014751 | A1 | 1/2018 | Hill et al. |
| 2020/0001048 | A1* | 1/2020 | Oren ..................... A61B 17/00 |
| 2020/0338351 | A1* | 10/2020 | Panken |
| 2021/0260392 | A1* | 8/2021 | Postlewait ............. A61B 5/316 |
| 2022/0330969 | A1* | 10/2022 | Shih ............... A61B 17/320068 |
| 2022/0346663 | A1* | 11/2022 | Agnew .................. A61B 5/062 |

* cited by examiner

RELIABILITY DETERMINATION OF ELECTRODE LOCATION DATA

CROSS-REFERENCE TO RELATED APPLICATIONS

This application is a continuation of U.S. application Ser. No. 16/456,439, filed 28 Jun. 2019 (the '439 application), now U.S. Pat. No. 10,967,147. This application claims the benefit of U.S. provisional application No. 62/691,275, filed 28 Jun. 2018, (the '275 application). The '439 application and '275 application are both hereby incorporated by reference as though fully set forth herein.

BACKGROUND a. Field of the Invention

The present disclosure relates generally to determining a reliability of location data received from an electrode.

b. Background Art

Medical devices, catheters, and/or cardiovascular catheters, such as electrophysiology catheters can be used in a variety of diagnostic, therapeutic, mapping and/or ablative procedures to diagnose and/or correct conditions such as atrial arrhythmias, including for example, ectopic atrial tachycardia, atrial fibrillation, and atrial flutter. A medical device can be threaded through a vasculature of a patient to a site where the diagnostic, therapeutic, mapping, and/or ablative procedure to diagnose and/or correct the condition is performed.

Sensors (e.g., electrodes, magnetic positioning sensors) can be placed on the medical device, which can receive signals that are generated proximate to the patient from a device. Based on the received signals, an orientation and/or position of the medical device within a heart can be computed.

One technique for determining the position and orientation of a catheter within a body is by tracking a plurality of sensors on the catheter using a position sensing and navigation system (sometimes called a location mapping system). The sensors can include electrodes disposed on the catheter, which can provide voltage measurements associated with their exposure to an electrical field generated through excitation of pairs of electrodes on an outer surface of the body. Voltage measurements on the catheter electrodes can then be used to determine the position and orientation of the catheter electrodes within a coordinate system of the position sensing and navigation system. Other exemplary position sensing and navigation systems include magnetic systems.

In order to provide information to clinicians about the position and orientation of the catheter, the determined position and orientation of the catheter sensors is often used to render an image of the catheter relative to surrounding tissues, including heart tissues. One drawback to conventional systems, however, is that the determined position and orientation of the catheter sensors can include errors due to errors associated with data received from the catheter electrodes. For example, some of the catheter electrodes may be misconnected, may be disconnected, and/or may be faulty. These errors can distort the rendered shape of the catheter from its true mechanical shape in the resulting image.

SUMMARY

Embodiments of the present disclosure include a system for determining an error associated with an electrode disposed on a medical device. The system comprises a processor and a memory storing instructions on a non-transitory computer-readable medium. The instructions are executable by the processor to receive an electrode signal from the electrode disposed on the medical device. The instructions are further executable by the processor to receive a plurality of other electrode signals from a plurality of other electrodes disposed on the medical device. The instructions are further executable by the processor to determine that the electrode signal received from the electrode disposed on the medical device is an outlier in relation to the plurality of other electrode signals from the plurality of other electrodes disposed on the medical device, based on a comparison between the electrode signal and the plurality of other electrode signals.

Embodiments of the present disclosure include a method for determining an error associated with an electrode disposed on a medical device. The method can comprise receiving an electrode signal from the electrode disposed on the medical device. The method can comprise receiving a plurality of other electrode signals from a plurality of other electrodes disposed on the medical device. The method can comprise determining impedance based coordinates for the electrode from the electrode signal and for the plurality of other electrodes from the plurality of other electrode signals. The method can comprise determining that the impedance based coordinates for the electrode disposed on the medical device is an outlier in relation the plurality of other impedance based coordinates for the plurality of other electrodes disposed on the medical device, based on a comparison between the impedance based coordinates for the electrode and the plurality of other impedance based coordinates for the plurality of other electrodes. The method can comprise excluding the impedance based coordinates for the electrode disposed on the medical device that is determined to be an outlier in determination of a shape of the catheter.

Embodiments of the present disclosure include a system for determining an error associated with an electrode disposed on a medical device. The system comprises a processor and a memory storing instructions on a non-transitory computer-readable medium. The instructions are executable by the processor to acquire data points corresponding to measured positions of a plurality of electrodes disposed on the medical device. The instructions are further executable by the processor to parameterize the catheter to determine true positions of the plurality of electrodes disposed on the medical device. The instructions are further executable by the processor to calculate synthetic parameters from the measured positions of the plurality of electrodes and the true positions of the plurality of electrodes. The instructions are further executable by the processor to filter the synthetic parameters. The instructions are further executable by the processor to generate the smoothed image of the catheter using the filtered synthetic parameters.

DETAILED DESCRIPTION

Figure 1:
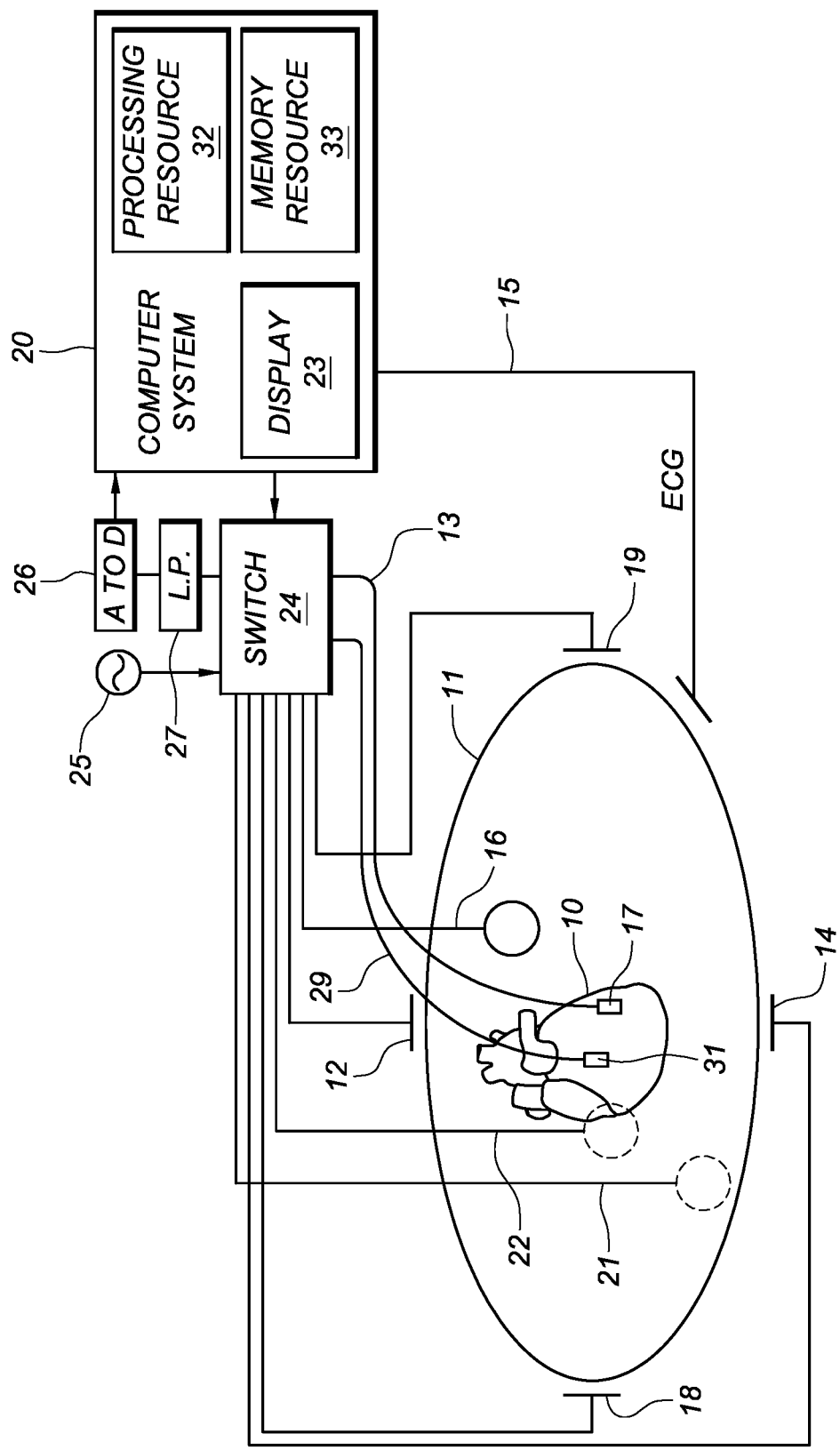
FIG. 1 is a diagrammatic view of an exemplary system for performing one or more diagnostic or therapeutic procedures, wherein the system comprises an impedance based medical positioning system, in accordance with embodiments of the present disclosure.

Referring now to the drawings wherein like reference numerals are used to identify identical components in the various views, FIG. 1 is a diagrammatic overview of a catheter system in which the invention may be practiced. The system may comprise various visualization, mapping and navigation components as known in the art, including among others, for example, an EnSite™ Velocity™ Cardiac Mapping and Visualization System commercially available from St. Jude Medical, Inc., or as seen generally by reference to U.S. Pat. No. 7,263,397, owned by the common assignee of the present invention, and hereby incorporated by reference in its entirety.

The system may be used in connection with or for various medical procedures, for example, mapping of the heart and/or cardiac ablation procedures. In one embodiment, the medical positioning system 14 may comprise a magnetic field-based system such as, for example, the Carto™ System available from Biosense Webster, and as generally shown with reference to one or more of U.S. Pat. Nos. 6,498,944; 6,788,967; and 6,690,963, the entire disclosures of which are incorporated herein by reference, or the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference. Alternatively, the medical positioning system 14 may comprise a combination magnetic field-based system and electric field-based system such as, for example and without limitation, the Carto 3™ System also available from Biosense Webster. Although reference is made to cardiac mapping of the heart, one or more aspects of the present disclosure may apply to other anatomic structures.

With reference to FIG. 1, the catheter system includes a diagrammatic depiction of a heart 10 of a patient 11. The system includes the ability to receive a plurality of catheter locations as the catheter distal end is swept around and within a chamber of the heart. For this purpose, FIG. 1 shows an exemplary catheter localization system of the type based on externally-applied orthogonal electric fields which are used to determine the location of one or more catheter position sensors. Such a system is known generally in the art (e.g., an EnSite NAVX™ Navigation and Visualization System). It should be understood, however, that this embodiment is exemplary only and not limiting in nature. Other technologies for determining the location in 3D space of a catheter, such as the MediGuide™ system, may be used in practicing the present invention, including for example, the CARTO navigation and location system of Biosense Webster, Inc., or the AURORA® system of Northern Digital Inc., both of which utilize magnetic fields rather than electrical fields. Accordingly, as used herein, a sensor is provided for producing signals indicative of catheter location information, and may include one or more position sensors. The position sensors can include one or more electrodes configured to detect one or more characteristics of an electrical field, for example in the case of an impedance-based localization system, or alternatively, one or more coils (e.g., wire windings) configured to detect one or more characteristics of a magnetic field, for example, in the case of a magnetic-field based localization system.

It should be further understood that in some localization systems, one or more position sensors may collectively define the sensor. The one or more position sensors may be provided on a distal end of a catheter and the localization system may be configured to obtain location information from the one or more position sensors. The localization system may compute a distal location of the catheter using not only the received location information, but also a geometrical relationship between the one or more position sensors providing the location information and the distal location on the catheter (e.g., one piece of geometrical information may be the ring electrode to tip distance). Finally, the localization system may use the computed location, as if it were collected directly. Likewise, in a magnetic field based localization embodiment, the catheter tip and the magnetic coil may have a geometrical relationship therebetween where the localization system is configured to use the computed tip location (i.e., computed based on the magnetic coil signals and predefined knowledge of the geometrical relationship between coil and tip) as if such location were collected directly. Of course, other variations are possible.

With continued reference to FIG. 1, in the illustrated impedance-based localization system embodiment, three sets of surface electrodes (e.g., applied via a patch) are shown: X-axis electrodes 12, 14; Y-axis electrodes 18, 19; and Z-axis electrodes 16, 22. Additionally, an additional surface electrode 21 (e.g., applied via a "belly" patch) may be used. The surface electrodes are all connected to a switch 24. A representative catheter 13 is shown, which has a single distal electrode 17, which may be referred to herein as a "roving" or "measurement" electrode. In some embodiments, the catheter 13 can be a coronary sinus catheter or a right ventricle apex catheter. The electrode 17 may define the position sensor in this embodiment, but as alluded to above, many variations are possible and the catheter 13 can include multiple position sensors, as discussed further herein. FIG. 1 also shows a second, independent catheter 29 with a fixed reference electrode 31, which may be stationary on the heart 10 for calibration purposes.

FIG. 1 further shows a computer system 20, a signal generator 25, an analog-to-digital converter 26 and a low-pass filter 27. The computer system 20 can utilize software, hardware, firmware, and/or logic to perform a number of functions described herein. The computing system 20 can be a combination of hardware and instructions to share information. The hardware, for example can include processing resource 32 and/or a memory resource 33 (e.g., non-transitory computer-readable medium (CRM) database, etc.). A processing resource 32, as used herein, can include a number of processors capable of executing instructions stored by the memory resource 33. Processing resource 32 can be integrated in a single device or distributed across multiple devices. The instructions (e.g., computer-readable instructions (CRI)) can include instructions stored on the memory resource 33 and executable by the processing resource 32 for aligning a cardiac model.

The computer system 20 is configured to control the signal generator 25 in accordance with predetermined strategies to selectively energize various pairs of surface electrodes. In operation, the computer system 20 is configured to obtain raw patch data (i.e., voltage readings) via the filter 27 and A-D converter 26 and use this raw patch data to determine the raw electrode location coordinates in three-dimensional space (X, Y, Z) of a catheter electrode positioned inside the heart 10 or chamber thereof (e.g., such as the roving electrode 17 mentioned above). In some embodiments, a phase of the patient's 11 cardiac cycle can be measured or otherwise determined when such electrode location coordinates are being received. For this purpose, in an embodiment, most or all of the conventional twelve (12) ECG leads, coupled to body surface electrodes and designated collectively by reference numeral 15, are provided to support the acquisition of an electrocardiogram (ECG) of the patient 11.

Alternatively, a reference electrode positioned in a fixed location in the heart 10, such as fixed reference electrode 31, may be used to provide a relatively stable signal that can be analyzed to determine the cardiac phase of the heart 10 in the cardiac cycle (e.g., placed at the coronary sinus). More generally, another catheter having an electrode, other than the moving or roving catheter, may be placed and maintained in a constant position relative to the heart 10 to obtain a relatively stable signal indicative of cardiac phase. As shown, the ECG leads 15 are coupled directly to the computer system 20 for acquisition and subsequent processing to obtain the phase of the heart 10 in the cardiac cycle. The ECG leads 15 may also be provided to other systems (not shown).

As previously mentioned, embodiments of the present disclosure can be used with a magnetic field-based system. Some embodiments can include a main electronic control unit (e.g., one or more processors) having various input/output mechanisms, a display, an optional image database, a localization system such as a medical positioning system (MPS) (electromagnetic sensor tracking system), an electrocardiogram (ECG) monitor, one or more MPS location sensors (e.g., patient reference sensor), and an MPS-enabled medical device (such as an elongated catheter or introducer) which itself includes one or more of the above-described MPS location sensors. As discussed, in some embodiments, the medical positioning system may comprise a magnetic field-based system such as, for example, the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference.

Embodiments can include input/output mechanisms, which can comprise conventional apparatus for interfacing with a computer-based control unit, for example, a keyboard, a mouse, a tablet, a foot pedal, a switch or the like. Embodiments can also include a display, which can also comprise conventional apparatus.

Embodiments may find use in navigation applications that use imaging of a region of interest. Therefore, the magnetic field-based system may optionally include an image database. The image database may be configured to store image information relating to the patient's body, for example, a region of interest surrounding a destination site for the medical device and/or multiple regions of interest along a navigation path contemplated to be traversed by the device to reach the destination site. The image data in the image database may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus) wherein the image database acts as a buffer (live fluoroscopy); and/or (3) a sequence of related two-dimensional images defining a cine-loop (CL), wherein each image in the sequence has at least an ECG timing parameter associated therewith adequate to allow playback of the sequence in accordance with acquired real-time ECG signals obtained from the ECG monitor. It should be understood that the foregoing are examples only and not limiting in nature. For example, the image database may also include three-dimensional image data. It should be further understood that the images may be acquired through any imaging modality, now known or hereafter developed, for example X-ray, ultra-sound, computerized tomography, nuclear magnetic resonance or the like.

The MPS can be configured to serve as the localization system and therefore to determine positioning (localization) data with respect to one or more of MPS location sensors, one or more medical devices, and/or on one or more patient reference sensors (PRS), and output a respective location reading. The location readings may each include at least one or both of a position and an orientation (P&O) relative to a reference coordinate system, which may be the coordinate system of the MPS. For example, the P&O may be expressed as a position (i.e., a coordinate in three axes X, Y, and Z) and orientation (i.e., an azimuth and elevation) of a magnetic field sensor in a magnetic field relative to a magnetic field generator(s) or transmitter(s).

The MPS determines respective locations (i.e., P&O) in the reference coordinate system based on capturing and processing signals received from the magnetic field sensors, while such sensors are disposed in a controlled low-strength AC magnetic field. From an electromagnetic perspective, these sensors develop a voltage that is induced on the coil residing in a changing magnetic field, as contemplated here. The sensors are thus configured to detect one or more characteristics of the magnetic field(s) in which they are disposed and to generate an indicative signal, which is further processed by the MPS to obtain a respective P&O of the sensors. Exemplary design features and manufacturing processes and methods for the sensors and medical devices incorporating such sensors may be found in U.S. Pat. No. 8,636,718, the entirety of which is incorporated by reference herein.

The MPS sensor, and optionally additional MPS sensors in further embodiments, may be associated with the MPS-enabled medical device. Another MPS sensor, namely, a patient reference sensor (PRS) is configured to provide a positional reference of the patient's body so as to allow motion compensation for gross patient body movements and/or respiration-induced movements. The PRS may be attached to the patient's manubrium sternum, a stable place on the chest, or another location that is relatively positionally stable. Like MPS location sensor, the PRS is configured to detect one or more characteristics of the magnetic field in which it is disposed, wherein the MPS provides a location reading (e.g., a P&O reading) indicative of the PRS's position and orientation in the reference coordinate system.

The electro-cardiogram (ECG) monitor is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit for ECG synchronized playback of a previously captured sequence of images (cine loop) stored in the database. The ECG monitor and the ECG-electrodes may both comprise conventional components.

The magnetic field-based system can be incorporated into or associated with a fluoroscopic imaging system, which may include commercially available fluoroscopic imaging components, for example, an x-ray source, a C-Arm, and/or an x-ray image intensifier or detector (i.e., "Catheter Lab"). The MPS (electromagnetic sensor tracking system) includes a magnetic transmitter assembly (MTA) (electromagnetic field generator) and a magnetic processing core for determining location (P&O) readings. The MTA is configured to generate the magnetic field(s) in and around the patient's chest cavity, in a predefined three-dimensional space identified as a motion box. The MPS sensors are, as described above, configured to sense one or more characteristics of the magnetic field(s) when the sensors are in a motion box, and each generate a respective signal that is provided to the magnetic processing core. The processing core is responsive to these detected signals and is configured to calculate respective P&O readings for each MPS sensor in the motion box. The processing core can detect when an MPS sensor exits the motion box. Thus, the MPS enables real-time tracking of each sensor in three-dimensional space. The actual volume of the motion box may be stored in, for example, the processing core, and processing core is able to determine the positions and orientations of each sensor in relation to the boundaries of motion box. Alternatively, the actual volume of motion box may be stored in, for example, the main control, and the main control may be able to determine the positions and orientations of each sensor in relation to the boundaries of the motion box. Accordingly, the system can evaluate (e.g., in the processing core or in the main control) whether a sensor is within, at the boundary of, or outside of the motion box. Based on this information, the motion box and sensor(s) can be displayed in relation to one another on the display as described in greater detail elsewhere herein.

In some alternative embodiments, the MTA can be located underneath a patient examination table, between an x-ray source and the patient examination table. For example, the MTA can be connected with the patient examination table. In some embodiments, as discussed herein, the MTA can be a mobile device, which can be placed on a chest of the patient and used to generate the magnetic field for tracking of the object.

The positional relationship between the image coordinate system and the MPS reference coordinate system (electromagnetic tracking coordinate system) may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in the database), a registration step registering the MPS coordinate system and the image coordinate system may need to be performed so that MPS location readings can be properly coordinated with any particular image being used.

Figure 2A:
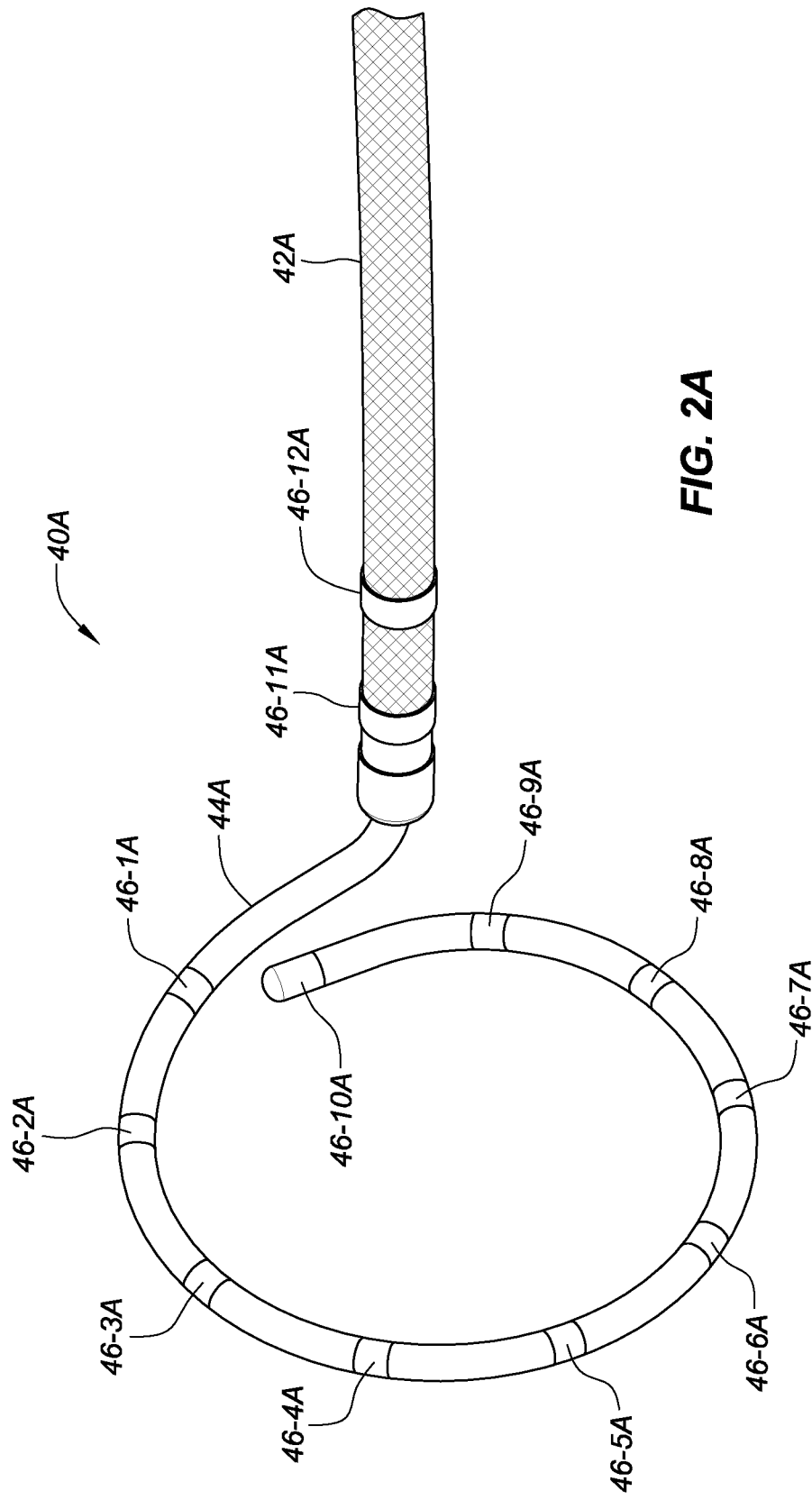
FIG. 2A depicts an electrophysiology catheter, in accordance with embodiments of the present disclosure.

FIG. 2A depicts an electrophysiology catheter 40A, in accordance with embodiments of the present disclosure. The electrophysiology catheter 40A can be used in an electrophysiology procedure to help doctors understand a nature of abnormal heart rhythms (e.g., arrhythmias). The procedure is performed by inserting the electrophysiology catheter 40A, which measures electrical activity, through blood vessels that enter the heart. Each electrophysiology catheter 40A can include several electrodes 46-1A, 46-2A, . . . , 46-12A connected to a computer system (e.g., computer system 20 in FIG. 1) via a connection box. Hereinafter, the electrodes 46-1A, 46-2A, . . . , 46-12A are referred to in the plural as electrodes 46A.

Although not depicted, the electrophysiology catheter 40A can include a magnetic position sensor (not depicted), in some embodiments. The electrodes can detect one or more characteristics of an electrical field in which the electrodes 46A are disposed. As previously discussed herein, in relation to FIG. 1, the electrical field can be produced by surface electrodes (e.g., patch electrodes) placed on an exterior of the patient. Based on the impedances associated with signals received from the electrodes 46A, a position (e.g., coordinates) of the electrophysiology catheter 40A can be determined. In some embodiments, the electrophysiology catheter 40A can be an Advisor™ FL Circular Mapping Catheter, Sensor Enabled™, as produced by St. Jude Medical, Inc., although the electrophysiology catheter 40A can be another type of electrophysiology catheter in some embodiments. The catheter 40A can be used in conjunction with an EnSite™ Velocity™ Cardiac Mapping and Visualization System and/or a MediGuide™ system, among other types of systems, for example those mentioned herein.

However, in some embodiments, the coordinates of one or more of the electrodes 46 on the electrophysiology catheter can be outliers (i.e., incorrect), because of faulty electrodes, disconnected electrodes, and/or misconnected electrodes, etc. Because the coordinates of the electrodes 46A are used in a determination of an overall position of the electrophysiology catheter, the determined position of the electrophysiology catheter 40A can be incorrect. The consequences of determining an incorrect position for an electrophysiology catheter 40A can provide for negative results in procedures that utilize the electrophysiology catheter 40A. Embodiment of the present disclosure can detect outliers and prevent incorrect measurements from being used in the determination of the position of the electrophysiology catheter 40A.

Figure 2B:
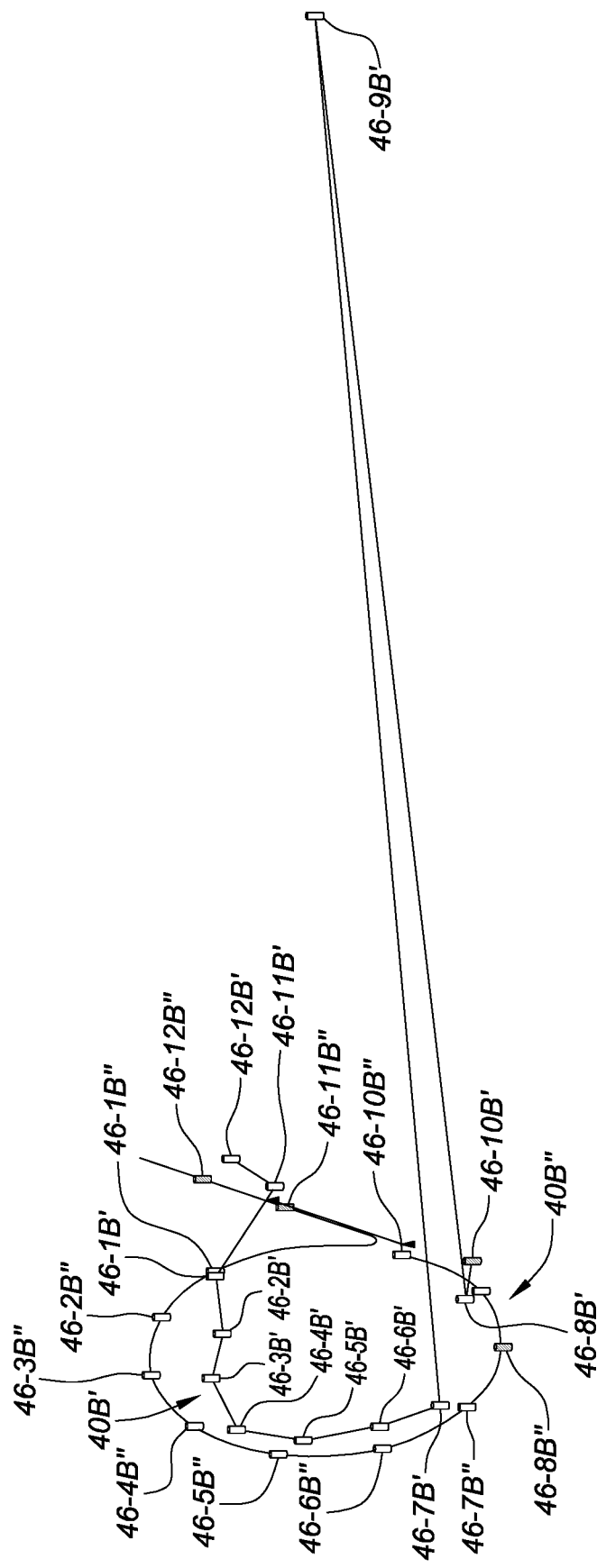
FIG. 2B depicts an unfiltered graphical representation of unfiltered electrode positions that includes an unfiltered electrode position of a disconnected electrode and a filtered graphical representation of filtered electrode positions, in accordance with embodiments of the present disclosure.

FIG. 2B depicts an unfiltered graphical representation 40B' of unfiltered electrode positions 46-1B', 46-2B', . . . , 46-12B' that includes an unfiltered electrode position 46-9B' of a disconnected electrode 46-9A (FIG. 2A) and a filtered graphical representation 40B" of filtered electrode positions 46-1B", 46-2B", . . . , 46-12B", in accordance with embodiments of the present disclosure. Hereinafter, unfiltered electrode positions 46-1B', 46-2B', . . . , 46-12B' are referred to in the plural as unfiltered electrode positions 46B' and filtered electrode positions 46-1B", 46-2B", . . . , 46-12B" are referred to in the plural as filtered electrode positions 46B". In some embodiments, the unfiltered electrode positions 46B' and the filtered electrode positions 46B" can be associated with electrodes on an electrophysiology catheter 40A, as depicted in FIG. 2A. However, embodiments of the present disclosure can be used with catheters other than the catheter depicted in FIG. 2A.

Embodiments of the present disclosure can determine a location of the electrodes 46A disposed on the electrophysiology catheter 40A and can further determine whether one or more of the determined locations of the electrodes 46A are outliers (e.g., incorrect). If outliers exist, embodiments of the present disclosure can account for the outliers in determination of positions of the electrodes 46A and in determination of the overall position of the electrophysiology catheter 40A in whole. In some embodiments, an Extended Kalman Filter (EKF) can be used to process impedance based coordinates of the electrodes 40A to determine a position, shape, and/or orientation of the catheter. In some embodiments, unfiltered electrode positions 46B' can include outliers, which can have an effect on an accuracy when determining the position of the electrodes 46A and the electrophysiology catheter 40A in whole.

In some embodiments, if the data received from one of the electrodes 46A is deemed to be from an electrode 46A that is an outlier, the data (e.g., coordinates of the electrode 46A) can be excluded from the extended EKF input. In this way, the resulting catheter position, shape, and orientation are reliable and stable. In an example, outliers can be detected using ad hoc considerations, based on raw electrode impedance readings and coordinates (per se as well as in relationship to filtered coordinates). In some embodiments, an electrode 46A can be determined to be disconnected when an impedance associated with a signal received from the electrode 46A is different than and/or noisier than an impedance associated with signals received from electrodes 46A that are connected. For instance, impedances associated with signals received from electrodes 46A disposed on the electrophysiology catheter 40A can be compared to one another. Electrodes 46A producing signals with impedances that are different than an impedance associated with signals produced by other electrodes 46A can be indicated as outliers. For example, an average impedance associated with signals produced by electrodes 46A can be determined and each impedance associated with each individual signal produced by each individual electrode 46A can be compared to the average impedance. If the impedance associated with signals of one or more electrodes 46A varies (e.g., is greater than a defined threshold or is less than a defined threshold) with respect to the average impedance, then the coordinates of the one or more electrodes 46A can be indicated as an outlier. For example, in some embodiments, a determination can be made that the impedance associated with the electrode signal is an outlier in response to the difference between the electrode signal and the average impedance being greater than a defined threshold. In some embodiments, signals produced by electrodes 46A can be determined to outliers if their associated impedances are greater then or less than an impedance associated with signals produced by other electrodes 46A.

In some embodiments, coordinates of an electrode 46A can be determined to be an outlier as a result of the electrode 46A being disconnected. For example, the electrode 46A can be connected to a computer system 20 (FIG. 1) via a communication line (e.g., wire) that extends through a shaft of the catheter 40A and is connected to the computer system 20. In some embodiments, the communication line can be disconnected due to a problem with a connection port and/or the communication line. In some embodiments, the disconnected electrode's unfiltered electrode position 46B' can be located a particular distance away from the unfiltered electrode positions 46B' of other electrodes 46A. For instance, with respect to FIG. 2B, the unfiltered electrode position 46-9B' can be associated with an electrode 46-9A that has been disconnected.

In determination of whether each unfiltered electrode position 46B' is associated with an electrode 46A that has been disconnected, a distance between each one of the unfiltered electrode positions 46B' can be determined. As depicted in FIG. 2B, the unfiltered electrode position 46-9B' is associated with a disconnected electrode. The distance between each of the unfiltered electrode positions 46-9B' and neighboring unfiltered electrode positions 46-8B', 46-10B' can be compared to one another. If the distance between the unfiltered electrode position 46-9B' and its neighboring unfiltered electrode positions 46-8B', 46-10B' is greater than neighboring distances between other unfiltered electrode positions (e.g., the distance between unfiltered electrode position 46-6B' and its neighboring unfiltered electrode positions 46-5B', 46-7B' by a defined amount, then a determination can be made that the unfiltered electrode position 46-9B' is associated with a disconnected electrode. In an example, the unfiltered electrode position 46-9B' associated with the disconnected electrode can be several centimeters away from the neighboring unfiltered electrode positions 46-8B', 46-10B'.

In some embodiments, if the distance between the unfiltered electrode position 46-9B' and its neighboring unfiltered electrode positions 46-8B', 46-10B' is greater than a physically measured distance associated with the electrodes 46-8A, 46-9A, 46-10A, then the unfiltered electrode position 46-9B' can be determined to be an outlier. For example, a distance between the electrodes 46A disposed on the catheter 40A can be measured prior to the performance of a medical procedure. Based on the unfiltered electrode positions 46B', a distance between each one of the unfiltered electrode positions 46B' can be determined. If the distance between each one of the unfiltered electrode positions 46B' is greater than the physically measured distances between the 46A by a particular threshold, then a determination can be made that one or more of the unfiltered electrode positions 46B' are outliers.

In some embodiments, this threshold can be 1.5 times greater than the physically measured distance. In some embodiments, this threshold can be 5 times greater than the physically measured distance, although the threshold can be less than 1.5 times greater than the physically measured distance, greater than 5 times greater than the physically measured distance, or somewhere in between. As depicted in FIG. 2B, the distances between the unfiltered electrode position 46-9B' and the neighboring unfiltered electrode positions 46-7B', 46-8B' is much greater than the physically measured distance between the electrode 46-9A and the neighboring electrode 46-7A, 46-8A. As depicted, the distance between the unfiltered electrode position 46-9B' and the neighboring unfiltered electrode positions 46-7B', 46-8B' compared to the distance between the electrode 46-9A and the neighboring electrode 46-7A, 46-8A far exceeds a threshold of 1.5 and the threshold of 5. Accordingly, the unfiltered electrode position 46-9B' could be marked as an outlier and a determination can be made that the unfiltered electrode position 46-9B' is associated with a disconnected electrode. In some embodiments, when an unfiltered electrode position, as discussed herein, is determined to be an outlier, an indication can be provided to a physician that the an outlier exists and can particularly indicate what electrode 46A is the cause of the outlier. In the case of the unfiltered electrode position 46-9B', an indication can be provided to a user of the catheter 40A that the unfiltered electrode position 46-9B' is caused from the electrode 46-9A being disconnected. An indication can then be provided to a user to connect the disconnected electrode 46-9A and/or use a different catheter.

Figure 2C:
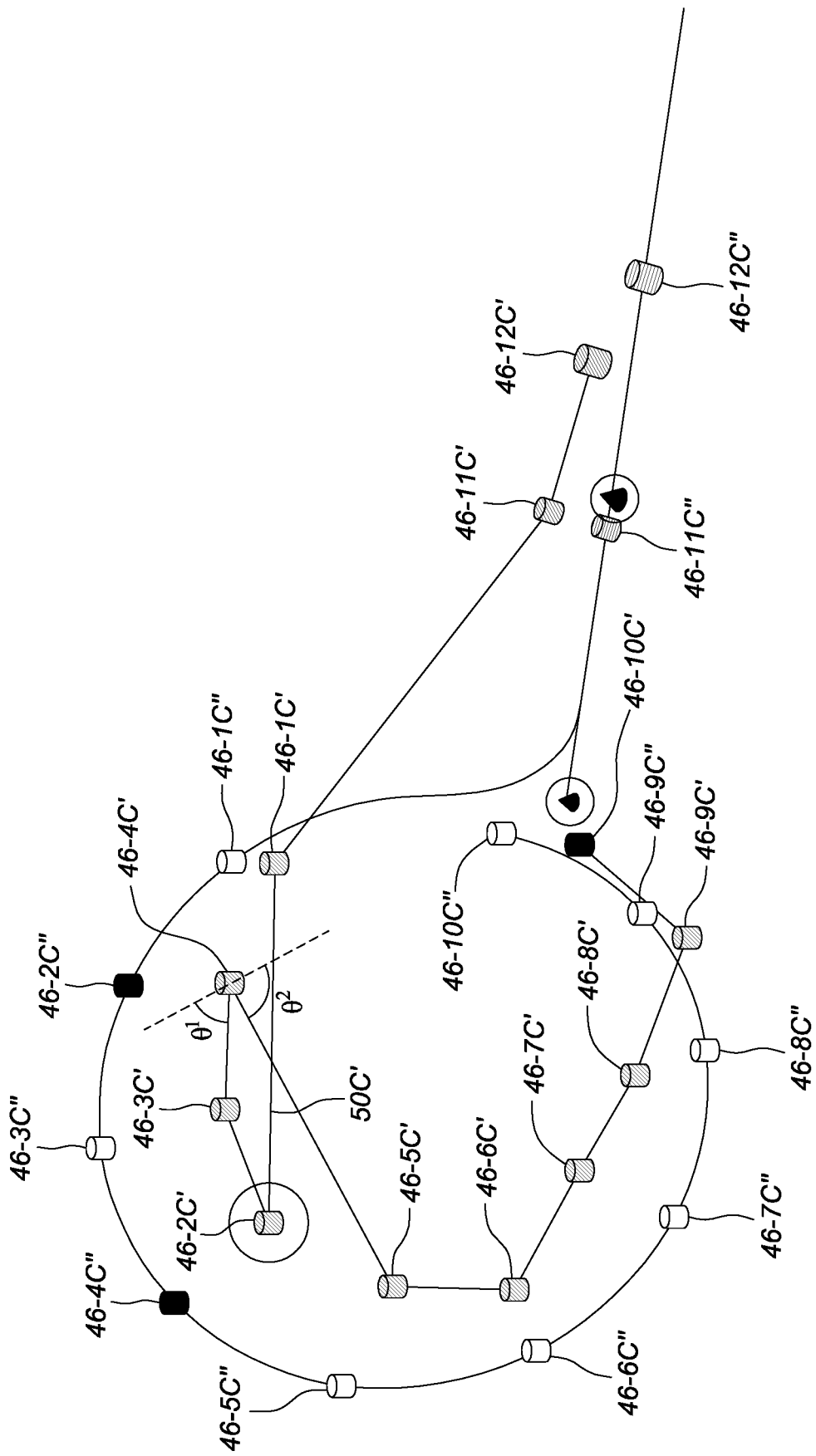
FIG. 2C depicts an unfiltered graphical representation of unfiltered electrode positions that includes an unfiltered electrode position of a misconnected electrode and a filtered graphical representation of filtered electrode positions, in accordance with embodiments of the present disclosure.

FIG. 2C depicts an unfiltered graphical representation 40C' of unfiltered electrode positions 46-1C', 46-2C', . . . , 46-12C' that includes an unfiltered electrode position 46-9C' of a misconnected electrode 42-2A, 46-4A (FIG. 2A) and a filtered graphical representation 40C" of filtered electrode positions 46-1C", 46-2C", . . . , 46-12C", in accordance with embodiments of the present disclosure. In some embodiments, an electrophysiology catheter 40A (FIG. 2A) can include one or more misconnected electrodes 46-2A, 46-4A. In an example, the electrodes 46A can each be connected to the computer 20 (FIG. 1) via respective connection ports (not depicted). In some embodiments, each electrode 46A can be assigned a connection port. Accordingly, an order of the electrodes 46A can be used in the calculation of coordinates based on the impedances.

In some embodiments, one or more of the electrodes 46A can be misconnected. In an example, the one or more misconnected electrodes 42-2A, 46-4A can be connected to the computer 20 via an incorrect connection port. For instance, a pair of electrodes 46A can be connected to the computer 20 via each other's connection port, resulting in a misconnected pair of electrodes 46-2A, 46-4A, which are reflected in the unfiltered electrode positions 46-2C', 46-4C'. For example, the second unfiltered electrode position 46-2C', is indicated as being located in a position between the third unfiltered electrode position 46-3C' and fifth unfiltered electrode position 46-5C', which is where the fourth unfiltered electrode position should be located; and the fourth unfiltered electrode position 46-4C', is indicated as being located in a position between the first unfiltered electrode position 46-1C' and third unfiltered electrode position 46-3C', which is where the second unfiltered electrode position should be located.

In an example, an unfiltered polyline 50C' can connect each one of the unfiltered electrode positions 46C. Because the second unfiltered electrode position 46-2C' and the fourth unfiltered electrode position 46-4C' have been swapped as a result of being misconnected, the unfiltered polyline 50C' extends from the first unfiltered electrode position 46-1C' past the third and fourth unfiltered electrode positions 46-3C', 46-4C' and can connect the first unfiltered electrode position 46-1C' and the second unfiltered electrode position 46-2C'. The polyline 50C' can then extend back to connect the third and fourth unfiltered electrode positions 46-3C', 46-4C' with the fifth unfiltered electrode position 46-5C'.

Based on an angle between each unfiltered electrode position and neighboring (e.g., adjacent) unfiltered electrode position, a determination can be made whether one of the unfiltered electrode positions is an outlier. For example, with reference to the fourth unfiltered electrode position 46-4C', an angle between its neighboring electrodes is approximately 150 degrees. For instance, the angle between the fourth unfiltered electrode position 46-4C' and its neighboring electrodes (e.g., third unfiltered electrode position 46-3C' and fifth unfiltered electrode position 46-5C' can be the sum of $\theta^1$ and $\theta^2$. As depicted, $\theta^1$ can be approximately 60 degrees and $\theta^2$ can be approximately 90 degrees, a total of which is 150 degrees.

In some embodiments, a determination can be made whether the angle between an unfiltered electrode position and its neighboring (e.g., adjacent) electrode positions is greater than a defined threshold. In an example, this threshold can be approximately two radians (e.g., 114.6 degrees). However, in some embodiments, the defined threshold can be greater than or less than two radians. As depicted in FIG. 2C, when the unfiltered electrodes are located on a same line, the angle between the unfiltered electrodes can be zero. In some embodiments, if the angle between the unfiltered electrode position and its neighboring electrode position is greater than the defined threshold, an indication can be provided to a physician that an outlier exists and can particularly indicate what electrode 46A is the cause of the outlier. In the case of the unfiltered electrode positions 46-2C' and 46-4C', an indication can be provided to a user of the catheter 40A that the unfiltered electrode positions 46-2C' and 46-4C' are caused from the electrodes 46-2C' and 46-4C' being misconnected. An indication can then be provided to a user to correctly connect the misconnected electrodes 46-2A and 46-4A or use a different catheter.

Some embodiments of the present disclosure can include a mechanism that can be utilized to prevent single noisy measurements produced by electrodes 46A from being determined as outliers. For example, a stack of a plurality of measurements (e.g., signals received from the electrodes 46A) can be stored. In some embodiments, a length between neighboring electrodes 46A can be determined based on the plurality of measurements and stored. For example, using the stack of the plurality of measurements, a plurality of lengths between each electrode 46A and neighboring electrodes 46A can be determined. In some embodiments, a lower threshold length can be defined (e.g., user definable) and an upper threshold length can be defined. In some embodiments, as discussed herein, outliers can be defined as electrodes where their distance to one of their neighbors differs significantly versus a prescribed distance.

The determined lengths can be compared to the lower threshold and the upper threshold and a determination can be made whether the determined lengths are lesser than the lower threshold, greater than the upper threshold, and/or between the lower threshold and upper threshold. Upon determination of whether the determined lengths are lesser than the lower threshold, greater than the upper threshold, and/or between the lower threshold and upper threshold, a number of the lengths that are less than the lower threshold or greater than the upper threshold can be determined. If the number of the lengths that are less than the lower threshold or greater than the upper threshold is above a defined amount then a determination can be made that the one or more electrodes associated with the length measurements are outliers. For example, if a fraction of the number of lengths that are lower than the lower threshold or greater than the upper threshold is above an upper fraction threshold, then a determination that the electrode 46A is an outlier can be made. If a fraction of the number of lengths that are less than the lower threshold or greater than the upper threshold is less than a lower fraction threshold, then a determination that the electrode 46A is normal can be made.

Figure 3:
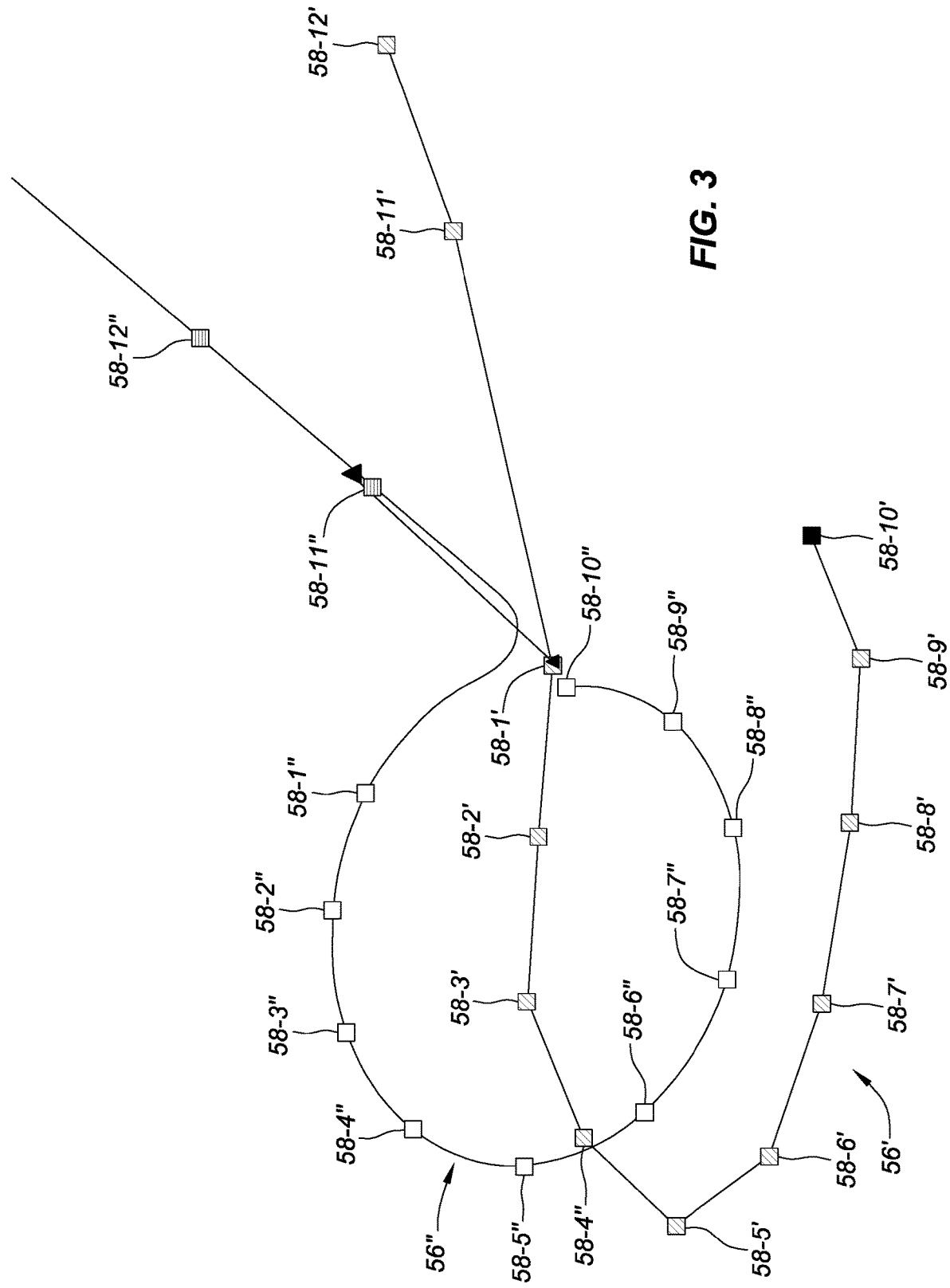
FIG. 3 depicts an unfiltered graphical representation of unfiltered electrode positions and a filtered graphical representation of filtered electrode positions, in accordance with embodiments of the present disclosure.

FIG. 3 depicts an unfiltered graphical representation 56' of unfiltered electrode positions 58-1', 58-2', . . . , 58-12' and a filtered graphical representation 56" of filtered electrode positions 58-1C", 58-2C", . . . , 58-12C", in accordance with embodiments of the present disclosure. Some embodiments of the present disclosure can provide for the recovery of an electrophysiology catheter's current shape, position, and orientation through use of several electrically conducting patches attached to the patient's body, such that each electrode can measure the impedance to the electric field induced between pairs of these patches; and additionally, by a magnetic field-based position and orientation sensor (e.g., magnetic position sensor) mounted on the catheter shaft, as discussed above, with respect to FIG. 2A. An extended Kalman filter (EKF) can be employed to reconstruct the catheter's geometry in a manner that is plausible, stable, and consistent with readings obtained from the electrodes and the position and orientation sensor.

Each electrophysiology catheter can be equipped with several electrodes, as well as a magnetic position and orientation sensor. The part of the catheter that is distal to the position and orientation sensor can be referred to as the flexible shaft and the more proximal part of the catheter that includes the magnetic position sensor can be referred to as the rigid shaft.

In some embodiments, readings from each electrode and sensor disposed on the catheter can be processed into a parametric description of the catheter's geometry. The parametric description of the flexible shaft can depend on the specific model of the catheter. For example, if the catheter is a variable-diameter steerable spiral loop, then the shape-related part of the parametric description of the catheter can include a current step of the spiral, a diameter of the spiral, and/or a deflection of the spiral from the rigid shaft. The geometry parameters from individual electrode and sensor readings can be fed into an extended Kalman filter. This filter can reconcile and smooth out the parameters, resulting in parameters that are geometrically plausible, temporarily stable, and consistent with electrode and sensor readings. In an example, the unfiltered electrode positions $58\text{-}1'$, $58\text{-}2'$, ..., $58\text{-}12'$ can be input into the extended Kalman filter, as discussed above, and filtered electrode positions $58\text{-}1C''$, $58\text{-}2C''$, ..., $58\text{-}12C''$ can be generated.

Figure 4:
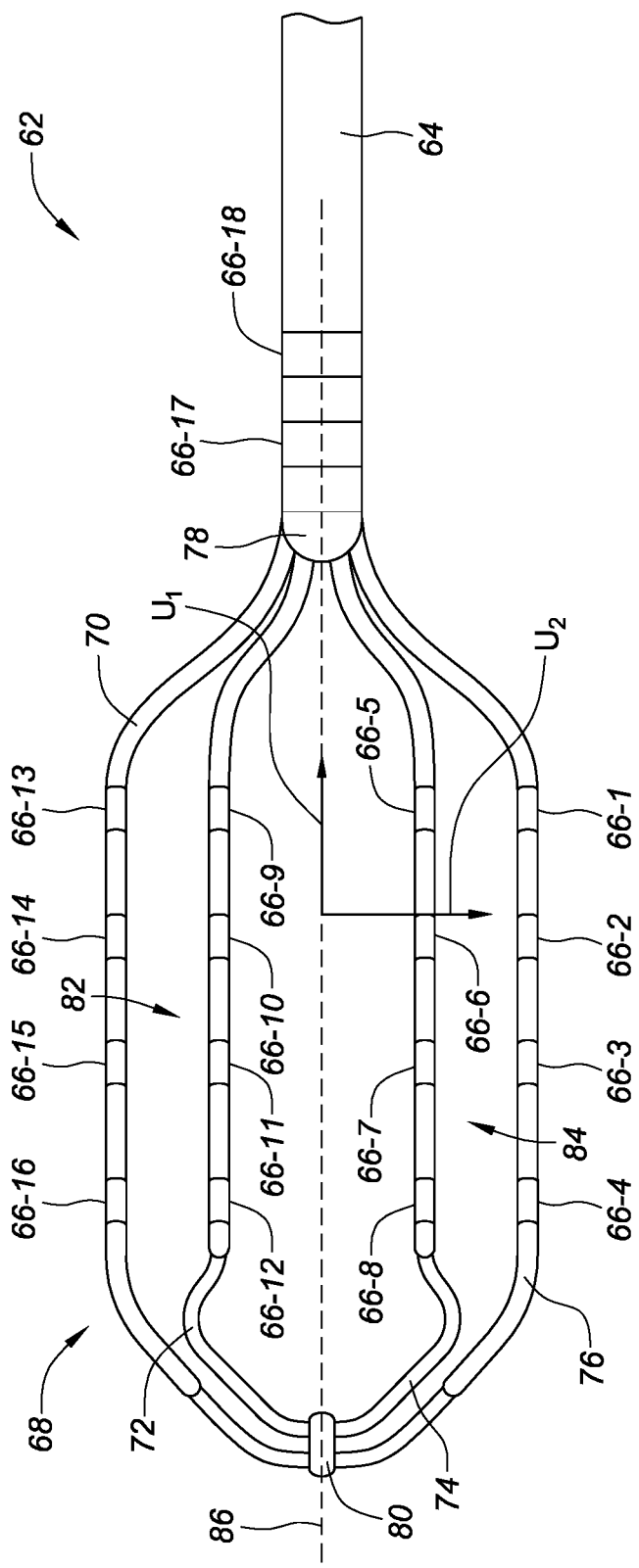
FIG. 4 depicts one embodiment of a planar catheter that may be used with the system shown in FIG. 1, in accordance with embodiments of the present disclosure.

FIG. 4 illustrates one embodiment of a planar catheter 62 that may be used with the system 20 shown in FIG. 1, in accordance with embodiments of the present disclosure. Catheter 62 comprises a catheter body 64 coupled to a paddle 68. Catheter body 64 can further comprise a first body electrode 66-18 and a second body electrode 66-17. Paddle 68 can comprise a first spline 70, a second spline 72, a third spline 74, and a fourth spline 76 that are coupled to catheter body 64 by a proximal coupler 78 and coupled to each other by a distal connector 80 at a distal end of paddle 68. In one embodiment, first spline 70 and fourth spline 76 can be one continuous segment, and second spline 72 and third spline 74 can be another continuous segment. In other embodiments the various splines can be separate segments coupled to each other. The plurality of splines can further comprise a varying number of electrodes 66-1, 66-2, ..., 66-16. The electrodes in the illustrated embodiment can comprise ring electrodes evenly spaced along the splines. In other embodiments the electrodes can be evenly or unevenly spaced and the electrodes can comprise point or other types of electrodes.

First spline 70, second spline 72, third spline 74, and fourth spline 76 generally lie in the same (topological) plane, generally indicated at 82. In other words, plane 82 is defined by a surface 84 of paddle 68 of catheter 62. Plane 84 includes a central axis 86. Although plane 82 is illustrated as relatively flat in FIG. 4, it should be understood that paddle 402 may bend, curl, buckle, twist, and/or otherwise deform. Accordingly, plane 82 defined by paddle 68 may correspondingly deform, such that plane 82 is a non-flat topological plane. As discussed further herein, the positions of electrodes 66-1, 66-2, ..., 66-16 may be described using a distance along a direction U1, a distal-to-proximal direction along central axis 86, and a direction U2, a direction from first spline 70 towards fourth spline 76.

Figure 5:
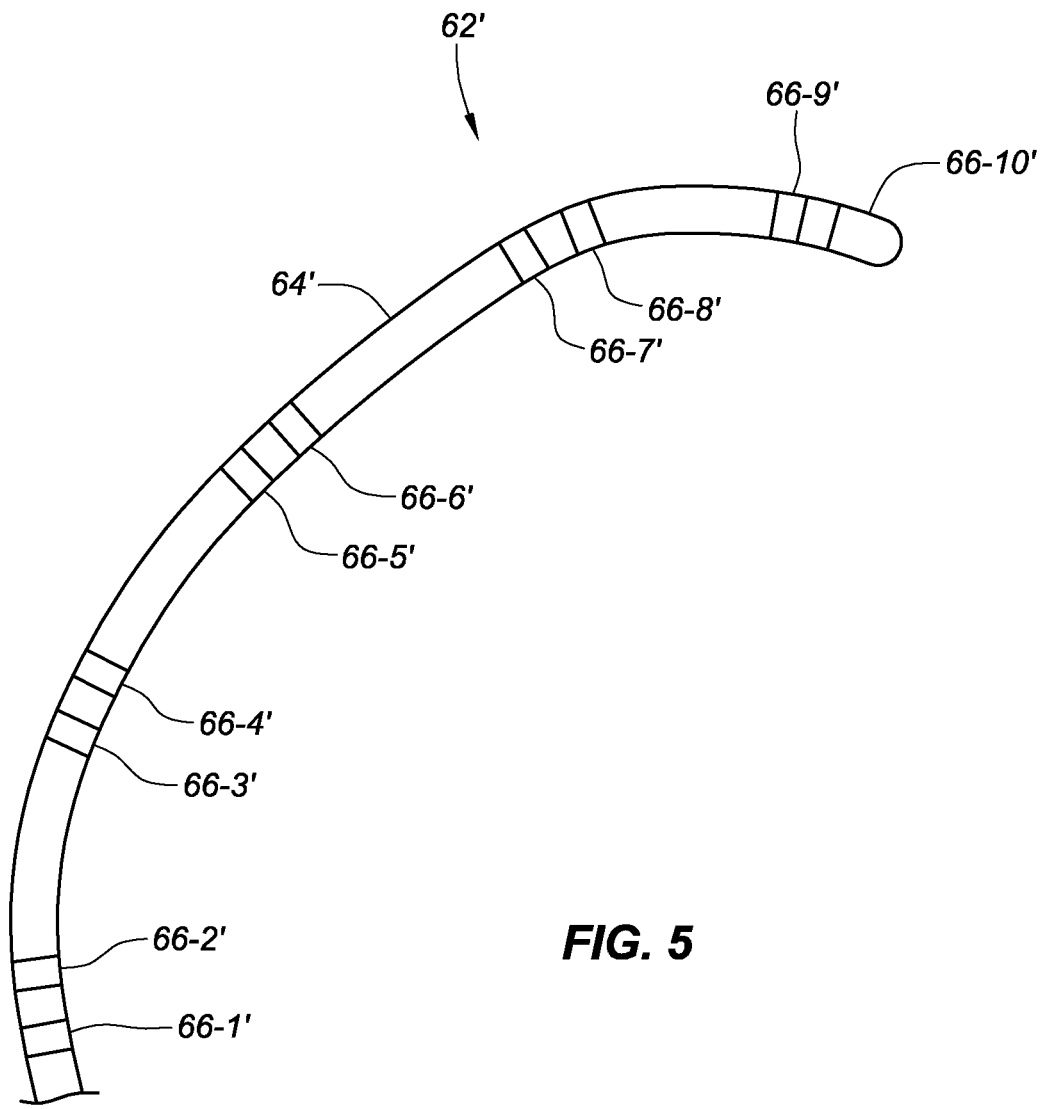
FIG. 5 depicts one embodiment of a curved catheter that may be used with the system shown in FIG. 1, in accordance with embodiments of the present disclosure.

FIG. 5 illustrates one embodiment of a curved catheter 62' that may be used with the system 20 shown in FIG. 1, in accordance with embodiments of the present disclosure. The curved catheter 6s' can include a curved catheter body 64' on which a plurality of electrodes 66-66-2', ..., 66-10' can be disposed. In some embodiments, the electrodes can be ring electrodes.

Figure 6:
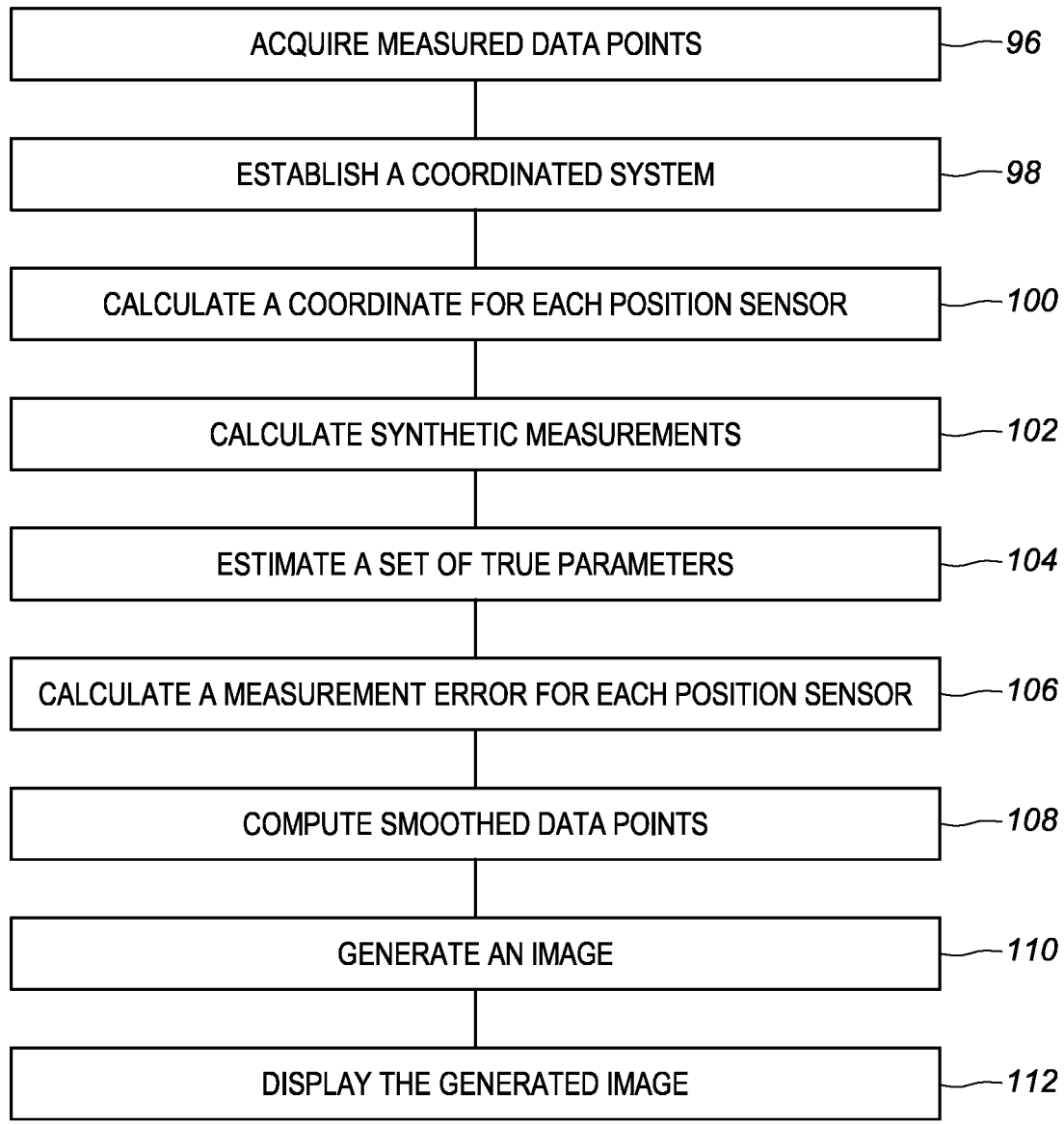
FIG. 6 depicts a method for generating a smoothed image of an elongate medical device in a body is illustrated, in accordance with embodiments of the present disclosure.

Referring to FIG. 6, a method for generating a smoothed image of an elongate medical device in a body is illustrated, in accordance with embodiments of the present disclosure. The method may be implemented in computer system 20 (e.g., in processing resource 32), as depicted in FIG. 1, for example, as software that configures the computer system 20 to perform the steps of the method. Aspects of the method are further discussed in U.S. Pub. No. 2018/0014751, which is hereby incorporated by reference, as though full set forth herein.

In a first step 96, measured data points corresponding to measured positions of each electrode 66-1, 66-2, ..., 66-18 on catheter, for example, catheter 62 as depicted in FIG. 4, are acquired. Electrode position measurements, like any measurement, may be expressed as a true position plus measurement error:

$$X = \langle + \rangle \in$$

where X represents the measured position of an electrode 66-1, 66-2, ..., 66-18 on catheter 62, $\langle X \rangle$ represents a true position of the electrodes 66-1, 66-2, ..., 66-18, and E represents the measurement error in the measured position, or the deviation from an idealized or true parametric form. If the error has zero mean over time, then temporal filtering may be used to remove the error. For catheter positions determined by measuring impedance values, such as in the EnSite™ Velocity™ system, there may be substantial electrode-specific errors that remain after temporal filtering. These remaining errors may be due to variations in manufacturing, local changes in the electrode-electrolyte interface, and/or uncompensated channel-to-channel variation in the instrumentation, among many other potential sources.

Measured positions of other points on the same catheter 62, such as measured positions of other electrodes 66-1, 66-2, ..., 66-18, can be used to reduce the remaining error in measured electrode positions. Though the true position, orientation, and/or shape of catheter 62 on which electrodes 66-1, 66-2, ..., 66-18 are disposed are not known, these may be inferred from a collection of the measured positions of electrodes 66-1, 66-2, ..., 66-18 on catheter 62. Generally, a "parameterized catheter 62" may refer to a catheter 62 for which a set of parameters (e.g., position, orientation, shape, length, number of electrodes 66-1, 66-2, ..., 66-18, distance between adjacent electrodes 66-1, 66-2, ..., 66-18, etc.) determine the true position of an electrode 66-1, 66-2, ..., 66-18.

In step 98, a coordinate system associated with catheter 62 (a "catheter coordinate system") is established. The individual electrode measurement errors can then be described as deviations from the true positions, as determined by the parameterized catheter and an inferred estimate of the true parameters, assuming that the measurement errors for each electrode 66-1, 66-2, ..., 66-18 are independent and normally distributed. The true parameters are estimated or inferred to be those parameters that minimize a sum of squared measurement errors between the parametrized position and the measured positions.

$$\langle x \rangle = \langle p \rangle, U_i)$$

where $\langle X_i \rangle$ represents the true position of electrode i, $\langle p \rangle$ represents a set of true parameters, and $U_i$ represents a coordinate in the catheter coordinate system for electrode i.

In step 100, coordinate $U_i$ for each electrode 66-1, 66-2, ..., 66-18 is calculated. For curved or linear one-dimensional catheters 62, $U_i$ is a scalar representing an arclength between the distal-most electrode (e.g., electrode 66-17) and electrode i along shaft 400 of catheter 62, and p is composed of a curve parameter and an affine transformation: $\{\theta, M\}$. The parametric form of catheter 62 can be described using the following:

$$f(p, U_i) = [1 \, U_i \cos(\theta U_i) \sin(\theta U_i)] M$$

This function defines the possible domain in which true positions of electrodes 66-1, 66-2, ..., 66-18 may lie. For curved or linear one-dimensional catheters, the true positions are described by a single curve of constant curvature, such that the true position of each electrode must fit a curve defined by curve parameter $\theta$ and affine projection M.

For an exemplary planar catheter 62, $U_i$ is a two-dimensional coordinate in plane 82 defined by surface 84 of catheter 62. A first term ($U_{i,1}$) specifies a distance in the distal to proximal direction $U_i$ along central axis 86 of catheter 62, and a second term ($U_{i,2}$) specifies a distance from central axis 86 perpendicular to central axis 86, for example, direction $U_2$. In addition, p is composed of a curvature term, a torsion term, and an affine transformation: $\{\kappa, \tau, M\}$. $\kappa$ and $\tau$ are constants over the plane defined by the surface of the catheter 62. Moreover, $$\theta^2 = \kappa^2 + \tau^2$$

such that the curve parameter is defined by the curvature term $\kappa$ and the torsion term $\tau$.

$$\mathcal{L}_{i,1} = \frac{U_{i,1}}{\sqrt{1 + \tau^2 U_{i,2}^2}}$$

$$\mathcal{L}_{i,2} = U_{i,2} - \frac{k}{\theta^2}$$

Each term $\mathcal{L}$ represents a correction in the distance measurements $U_{i,1}$, $U_{i,2}$ to account for any change in length that results from any curvature or twist (torsion) in the parametric plane defining catheter 62.

$$f(p, U_i) = [1 \, \mathcal{L}_{i,1} \mathcal{L}_{i,2} \cos(\theta \mathcal{L}_{i,1}) \mathcal{L}_{i,2} \sin(\theta \mathcal{L}_{i,1})] M$$

This function defines the possible domain in which true positions of electrodes 66-1, 66-2, ..., 66-18 may lie. For two-dimensional catheters, the true positions are described by an exemplary two-dimensional parametric form including curvature ($\kappa$) and torsion ($\tau$) terms.

In step 102, synthetic parameters can be calculated. Because the relationship between the measured data points and the true parameters can be highly non-linear, calculation of the computed data points used in the smoothed image of the elongate medical device can cause deterioration in the computed data points, resulting in an inaccurate smoothed image. In order to improve the accuracy of which the computed data points are calculated, one or more synthetic parameters can be calculated from the measured data points. The synthetic parameters can serve as an input to an extended Kalman filter in addition to the measured data points. The relationship between the synthetic parameters and the true parameters is very close to linear, thus causing the extended Kalman filter to perform much better. The step of calculating the synthetic parameters is catheter specific and can be performed for a planar catheter, as depicted and described in relation to FIG. 4, and/or a curved catheter as depicted and described in relation to FIG. 5. In an example, the synthetic parameters can be related to specific models of catheters.

In an example, with respect to the planar catheter, as depicted in FIG. 4, the synthetic parameters can be calculated by first estimating a direction of the distal part of the catheter 62 via the measured positions of the four distal electrodes 66-4, 66-8, 66-12, 66-16 by means of linear regression. The estimated plane in which the catheter 62 lies can be obtained from all of the measured positions of each electrode 66-1, 66-2, ..., 66-18 on catheter by means of principal component analysis. For example, in the estimated plane, for each pair of adjacent electrodes, an angle between the direction of the distal part of the catheter 62 and the direction of the pair of adjacent electrodes can be computed. For each pair of adjacent electrodes i, j, compute the pair direction $D_{ij} = X_i - X_j$; then project the directional vector of the distal part of the catheter 62 and the pair direction $D_{ij}$ onto the estimated plane and compute the angle between them. The synthetic parameters are the resulting set of angles. The calculation and use of the synthetic parameters improves an overall quality of the smoothed image, especially in cases where the catheter undergoes significant deformation from its relaxed state.

For the planar catheter 62 depicted in FIG. 4, the calculation of the synthetic parameters is as follows. Electrode position measurements are defined as follows:

$$X_i = \langle X_i \rangle + \epsilon$$

where $X_i$ represents the measured position of an electrode 66-1, 66-2, ..., 66-18 on catheter 62, $\langle X_i \rangle$ represents a true position of the electrodes 66-1, 66-2, ..., 66-18, and $\epsilon$ represents the measurement error in the measured position, or the deviation from an idealized or true parametric form. As described herein, the electrode position measurements $X_1$, $X_2$, ..., $X_{18}$ can correspond to the electrodes 66-1, 66-2, ..., 66-18. In some embodiments, the catheter body 64 direction DR can be computed as $X_{17} - X_{18}$ (i.e., the two electrodes 66-17, 66-18) disposed on the catheter body 64. The longitudinal axis direction $D_{LO}$ of the paddles can be computed as the average of single strut directions:

$$\tfrac{1}{4} \cdot ((X_1 - X_4) + (X_5 - X_8) + (X_9 - X_{12}) + (X_{13} - X_{16}))$$

The lateral axis direction $D_{LA}$ of the paddles can be computed as the average of the lateral quadruples:

$$\tfrac{1}{4} \cdot ((X_1 - X_{13}) + (X_2 - X_{14}) + (X_3 - X_{15}) + (X_4 - X_{16}))$$

For each pair of electrodes 66-1:66-2, 66-2:66-3, 66-3:66-4, 66-5:66-6, 66-6:66-7, 66-7:66-8, 66-9:66-10, 66-10:66-11, 66-11:66-12, 66-13:66-14, 66-14:66-15, 66-15:66-16, the direction vector $D_i = X_i - X_{i+1}$ can be computed. For each direction vector D the angle between it and the rigid shaft direction DR with respect to $D_{LA}$ can be computed with respect to the rotational axis, to provide 12 synthetic parameters. For each triple of electrodes 66-1:66-5:66-9, 66-5:66-9:66-13, 66-2:66-6:66-10, 66-6:66-10:66-14, 66-3:66-7:66-11, 66-7:66-11:66-15, 66-4:66-8:66-12, 66-8:66-12:66-16 the two lateral directions $DL_{i,1} = X_i - X_{i+4}$, $DL_{i,2} = X_{i+4} - X_{i+8}$ can be computed. For each couple of lateral directions $DL_{i,1}$, $DL_{i,2}$ the angle between them with respect to $D_{LO}$ as the rotational axis can be computed. These constitute a set of 8 more synthetic parameters. The method for computation of $D_{LO}$ and $D_{LA}$, as described above is accomplished via one possible method, however $D_{LO}$ and $D_{LA}$ can be calculated via other methodologies as well. For example, $D_{LO}$ and $D_{LA}$ can be calculated via linear regression. Although the above method for calculating the synthetic parameters applies to the planar catheter 62, synthetic parameters can also be computed for a curved catheter 62', for example, as depicted in FIG. 5. Although the computation of synthetic parameters for the planar catheter 62 and the curved catheter 62' are described herein, synthetic parameters can be determined for other types of catheters, as well, in a similar fashion.

With reference to the curved catheter depicted in FIG. 5, the calculation of the synthetic parameters are as follows. The rigid shaft origin and direction $O_R$, $D_R$ can be computed using the electrodes 66-1', 66-2', 66-3', 66-4' by means of a linear regression with the design matrix $$X = \begin{bmatrix} I_3 & I_3 & I_3 & I_3 \\ U_1 \cdot I_3 & U_2 \cdot I_3 & U_3 \cdot I_3 & U_4 \cdot I_3 \end{bmatrix} \in R^{12 \times 6}$$

$$\begin{bmatrix} O_R \\ D_R \end{bmatrix} = (X^T X)^{-1} X^T \cdot \begin{bmatrix} U_1 \\ U_2 \\ U_3 \\ U_4 \end{bmatrix}$$

The fitting plane normal N can be determined for the entire set $X_1, X_2, \ldots, X_{10}$ of electrode position measurements by means of Principal Component Analysis. As discussed herein, the electrodes 66-1', 66-2', ..., 66-10' can correspond to the electrode position measurements $X_1, X_2, \ldots, X_{10}$. For each pair of electrodes 66-4':66-5', 66-5':66-6', 66-6':66-7', 66-7':66-8', 66-8':66-9', 66-9':66-10' the direction vector $D_i = X_i - X_{i+1}$ can be computed. For each direction vector $D_i$ the angle between it and $D_R$ with respect to N as the rotational axis can be computed. This, therefore constitutes a set of 6 synthetic parameters and the three components of the normal N itself will represent another 3 synthetic parameters. As discussed above, with respect to the planar catheter 62, the method for computation of $D_R$ and N, as described above is accomplished via one possible method, however DR and N can be calculated via other methodologies as well.

With further reference to the method depicted in FIG. 6, in step 104, an estimate of the true parameters, p̂, as well as the synthetic parameters, discussed above, can be computed as a non-linear least-squares solution to the original measurements. Solvers such as Levenberg-Marquardt may be used for this purpose.

For all parameterized models, the measurement error ∈ is described by a thin-plate spline in the dimensionality of $U_i$, with a per-electrode stiffness specified by $\lambda_i$. "Stiffness" may be further described as a parameter that defines how much variation in the measured position of each electrode 66 is permitted. In other words, the larger the stiffness $\lambda$, the closer a smoothed position of that electrode 66 to the position corresponding to the inferred parameters ($U_i$). Shown below, the deviation of the smoothed positions from the measured positions ($\Lambda$) is a product of the stiffness and the difference between the measured positions and the positions resulting from the inferred parameters. In step 106, a measurement error for each electrode 66 (i.e., the measurement error in the measured position of each electrode 66) is calculated, based at least in part on stiffness parameter $\lambda_i$.

$$\in = (\Psi - \Lambda) W$$

$$\Psi_{ij} = \psi(|U_i - U_j|)$$

$$\Lambda_{ij} = \lambda_i \delta_{ij}$$

Typically, the radial basis function is defined as $\psi = r^3$ if $U_i$ is 1-D, $\psi(r) = r^2 \ln r$ if $U_i$ is 2-D and $\psi(r) = r$ if $U_i$ is 3-D. These radial basis functions are standard for thin plate splines. These are the functions for which $\nabla^4 \psi = 0$ over the entire domain. This form describes biharmonic functions. Biharmonic functions describe the physics of many continua including elastostatics or Stokes flows. In the thin plate spline formulation, the biharmonic function describes the bending of an isotropic body in which all the forces on the body sum to zero. In this sense, it is smooth. This physical description leads to the description of smoothing the errors.

For a given set of stiffness parameters $\lambda_i$, and an estimate of the true parameters, p̂, $\lambda$, the weights, W, are uniquely determined by solving the following equation:

$$(\Psi - \Lambda) W = X - f(\hat{p}, U_i)$$

In step 108, smoothed data points, $X_S$, are then computed based on (i) a function of the estimated set of true parameters—as estimated in step 104—and the respective coordinates of each of electrode 66—as calculated in step 100—as well as (ii) a smoothed fraction of the measurement error (i.e., $\Psi W$). More particularly, $X_S$ are calculated as follows:

$$X_S = f(\hat{p}, U_i) + \Psi W$$

In step 110, an image is generated based on smoothed data points $X_S$. In step 616, the generated image is displayed (e.g., on display 23, shown in FIG. 1). In some embodiments, the method depicted and discussed in relation to FIG. 6 can be used to determine the filtered graphical representation 56" in FIG. 3.

With further reference to FIG. 3, some embodiments of the present disclosure can determine a confidence associated with a projection of a catheter shape. For example, in a situation where a confidence in a catheter shape projected on a graphical user interface is low, then a physician should not trust the projection and should use other systems for better assessment. In some embodiments, a physical length of a the catheter can be determined. For example, each catheter can be associated with a physical length, which can be determined before an operation is performed. Depending on what type of catheter is used with the system described in FIG. 1, a different physical length can be associated with the catheter and recognized by the system.

The physical length of the catheter can be used to determine a confidence associated with the projection of the catheter shape. For example, the physical length of the catheter (e.g., mechanically measured) can be compared to a real time calculated length of the catheter, calculated from signals received from the electrodes (e.g., electrodes 46 in FIG. 2A) disposed on the catheter, using a filtered graphical representation of the catheter. In an example, the system can detect low confidence associated with the catheter shape where the real time calculated length of the catheter minus the physical length of the catheter is greater than a particular limit. In some embodiments where a low confidence associated with the projection of the catheter shape is determined, an indication can be provided to a user via a graphical user interface. For example, the projection of the catheter shape can glow a particular color (e.g., amber) on the graphical user interface.

In the determination of the real time length of the catheter, a real time length between each one of the electrode pairs (e.g., 58-12':58-11', 58-11':58-1', 58-1':58-2', 58-2':58-3', 58-3':58-4', 58-4':58-5', 58-5':58-6', 58-6':58-7', 58-7':58-8', 58-8':58-9', 58-9':58-10') can be determined and length between each pair can be summed to determine the overall real time length of the catheter, which can be compared to the physical length to determine the confidence associated with the projection of the catheter shape. In an example, as the overall real time length of the catheter decreases with respect to the physical length, the confidence associated with the projection of the catheter shape can go down. In a further example, as the overall real time length of the catheter increases with respect to the physical length, the confidence associated with the projection of the catheter shape can go down. In a particular example, where the physical catheter length is 70 millimeters and the overall real time catheter length is 90 millimeters, a difference between the physical catheter length and the overall real time catheter length is 20 millimeters, which can signify a low confidence associated with the projection of the catheter shape. In an example, as discussed above, if the difference between the physical catheter length and the real time length of the catheter is above the particular limit, a low confidence indication can be displayed to a user (e.g., physician) of the graphical user interface (e.g., display 23). By providing the indication to the user, the user is provided with a much better understanding if the projection is at a high and/or low confidence.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for reliability determination of electrode location data has been described above with a certain degree of particularity, those skilled in the art could make numerous alterations to the disclosed embodiments without departing from the spirit or scope of this disclosure. Further embodiments of the present disclosure will be apparent upon review of Appendix A. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system for determining a confidence associated with a projection of a catheter shape on a graphical user interface, the system comprising:
 a processor; and
 a memory storing instructions on a non-transitory computer-readable medium, wherein the instructions are executable by the processor to:
  determine a calculated length of the catheter based on one or more sensor signals received from the catheter;
  determine the confidence associated with the projection of the catheter shape by comparing the calculated length of the catheter to a known physical length of the catheter; and
  cause the confidence associated with the projection of the catheter shape to be displayed via the graphical user interface.

2. The system of claim 1, further comprising instructions executable by the processor to receive a plurality of electrode signals from a plurality of electrodes disposed on the catheter.

3. The system of claim 2, further comprising instructions executable by the processor to determine impedance based coordinates for the plurality of electrode signals.

4. The system of claim 3, further comprising instructions executable by the processor to determine the length of the projection of the catheter shape based on the impedance based coordinates for the plurality of electrode signals.

5. The system of claim 4, wherein the instructions executable by the processor to compare the real time calculated length of the projection of the catheter shape with the physical length of the catheter includes instructions to determine a difference between the calculated length of the projection of the catheter shape based on a sum of the lengths between each one of the impedance based coordinates and the known physical length of the catheter.

6. The system of claim 1, further comprising instructions executable by the processor to display an indication on the graphical user interface in response to the confidence being greater than a threshold.

7. The system of claim 1, further comprising instructions executable by the processor to display an indication on the graphical user interface in response to the confidence being less than a threshold.

8. The system of claim 1, wherein the physical length of the catheter is determined prior to a procedure.

9. The system of claim 1, further comprising instructions executable by the processor to:
receive a selection of a type of catheter from a user; and
associate a physical length with the type of catheter based on values stored in the memory.

10. The system of claim 1, further comprising instructions executable by the processor to compare the calculated length of the projection of the catheter shape with the physical length of the catheter using a filtered graphical representation of the catheter.

11. The system of claim 1, further comprising instructions executable by the processor to detect low confidence associated with the catheter shape when the calculated length of the projection of the catheter shape minus the physical length of the catheter is greater than a particular limit.

12. The system of claim 11, further comprising instructions executable by the processor to cause the projection of the catheter shape to glow, in response to detection of low confidence associated with the catheter shape.

13. A system for determining a confidence associated with a projection of a catheter shape on a graphical user interface, the system comprising:
a processor; and
a memory storing instructions on a non-transitory computer-readable medium, wherein the instructions are executable by the processor to:
receive a plurality of electrode signals from a plurality of electrodes disposed on the catheter;
determine impedance based coordinates for the plurality of electrode signals;
determine a calculated length of the catheter based on the impedance based coordinates;
determine the confidence associated with the projection of the catheter shape by comparing the calculated length of the catheter to a known physical length of the catheter; and
cause the confidence associated with the projection of the catheter shape to be displayed via the graphical user interface.

14. The system of claim 13, wherein the calculated length of the catheter is determined between pairs of the plurality of electrodes disposed on the catheter.

15. The system of claim 14, wherein a length between each pair of the plurality of electrodes is summed to determine the calculated length of the catheter.

16. The system of claim 13, wherein the confidence associated with the projection of the catheter shape is determined as decreasing in response to the calculated length decreasing with respect to the physical length.

17. The system of claim 13, wherein the confidence associated with the projection of the catheter shape is determined as decreasing in response to the calculated length increasing with respect to the physical length.

18. The method of claim 17, further comprising:
receiving a selection of a type of catheter from a user; and
associating a physical length with the type of catheter based on values stored in the memory.

19. The method of claim 17, further comprising detecting a low confidence associated with the catheter shape where the real time calculated length of the catheter minus the physical length of the catheter is greater than or less than a particular limit.

20. A method for determining a confidence associated with a projection of a catheter shape on a graphical user interface, the method comprising:
receiving a plurality of electrode signals from a plurality of electrodes disposed on a catheter;
determining impedance based coordinates for the plurality of electrode signals;
determining a calculated length of the catheter based on the impedance based coordinates using a summed distance between pairs of the plurality of electrodes;
determining the confidence associated with the projection of the catheter shape by comparing the calculated length of the catheter to the physical length of the catheter; and
indicating the confidence for the projection of the shape of the catheter via the graphical user interface.

* * * * *